United States Patent [19]

Toledo-Pereyra

[11] Patent Number: 4,502,295
[45] Date of Patent: Mar. 5, 1985

[54] ORGAN HYPOTHERMIC STORAGE UNIT

[75] Inventor: Luis H. Toledo-Pereyra, Grosse Pointe Farms, Mich.

[73] Assignee: Mount Carmel Research and Education Corporation, Detroit, Mich.

[21] Appl. No.: 582,033

[22] Filed: Feb. 21, 1984

[51] Int. Cl.³ .............................................. F25D 3/02
[52] U.S. Cl. ...................................... 62/463; 62/457; 62/306
[58] Field of Search ................... 62/64, 372, 463, 464, 62/530, 457, 306

[56] References Cited

U.S. PATENT DOCUMENTS

| | | | |
|---|---|---|---|
| 1,369,367 | 2/1921 | Thomson | 62/463 X |
| 1,451,917 | 4/1923 | Meyer | 62/463 X |
| 1,576,955 | 3/1926 | Dubraks | 62/463 X |
| 1,583,821 | 5/1926 | Willson | 62/463 |
| 3,106,074 | 10/1963 | Amburgey, Jr. | 62/464 |
| 3,777,507 | 12/1973 | Burton et al. | 62/306 |
| 3,810,367 | 5/1974 | Peterson | 62/64 X |
| 3,995,444 | 12/1976 | Clark et al. | 62/306 |
| 4,186,565 | 2/1980 | Toledo-Pereyra | 62/306 |
| 4,242,883 | 1/1981 | Toledo-Pereyra | 62/306 |

Primary Examiner—Lloyd L. King
Attorney, Agent, or Firm—Cullen, Sloman, Cantor, Grauer, Scott & Rutherford

[57] ABSTRACT

An organ hypothermic storage unit includes a first container with a removable cover and a plurality of organ receptacles mounted within the first container, each receptacle having a removable cover. A plurality of groups of spacers upon the container bottom wall receive and locate the receptacles spacing them from each other and from the container walls to define a chilling zone within the first container and around each receptacle. Each receptacle mounts upon its interior a thermometer. An outer container having a removable cover receives, supports and encloses the first container defining an insulating air space therebetween. The inner container is adapted to receive and store a quantity of ice within the chilling zone for continuously maintaining an organ in any receptacle at a temperature between 0° and 7° C., for maximal metabolic suppression and preservation thereof until transplant to a recipient. The containers, receptacles and covers thereof are of a clear transparent material.

9 Claims, 5 Drawing Figures

ORGAN HYPOTHERMIC STORAGE UNIT

BACKGROUND OF THE INVENTION

1. Field of the Invention

The present invention relates to the hypothermic storage of different organs and more particularly an organ hypothermic storage unit wherein a plurality of organs are nested within individual receptacles immersed within ice within a container for maintaining the organs before transplant at a predetermined temperature between 0° and 7° Centigrade (C) for maximal metabolic suppression and preservation thereof.

2. The Prior Art

Heretofore and after excision from a person or animal in the storage and preservation of organs for subsequent transplant to humans or animals various efforts have been made to chill and to maintain the organs at a low temperature above freezing. Chilled perfusion liquids have been pumped through the organs on a continuous basis, and means have been provided for maintaining the perfusion liquids at low temperatures below 10° C., for example. Heretofore perfusion of organs for subsequent transplant have been used with kidneys, liver, pancreas, lungs, hearts, small bowel or other organs capable of excision. This has been for maintaning the organs in a chilled condition above freezing for limited intervals utilizing perfusion apparatus.

Also in the procurement of organs and in their preservation at chilling temperatures for subsequent transplantation, procedures are required to guarantee a viable and functioning transplant wherein the transplant has been suitably preserved either by hypothermic mechanical perfusion or by hypothermic storage.

In both ways in order to keep an organ alive outside of the body, its metabolism must be reduced to such an extent that continued supply of oxygen and energy carriers will be unnecessary. It is recognized that if metabolism of an organ is suppressed to the maximum, the need for oxygen is minimized so that the organ can be stored for a limited period and preserved at chilling temperatures above freezing.

Most of the methods for preservation of organs for subsequent transplant contemplate the use of cooling in various manners and at various rates and at various temperatures and for maintaining such cooling over a period of time and with such other efforts as will maximize and suppress metabolism in the organ.

RELATED PATENT APPLICATION

A method of freezing and transplant of kidneys and apparatus therefore is disclosed in Applicant's copending patent application Ser. No. 499,560 filed May 31, 1983, now U.S. Pat. No. 4,471,629, issued Sept. 18, 1984.

SUMMARY OF THE INVENTION

An important feature of the present invention is to provide an organ hypothermic storage unit wherein one or more of a plurality of organs awaiting transplant to a recipient are individually stored within a receptacle within a first container to maintain them chilled by a packing of ice, around such receptacles at temperatures in the range of 0° to 7° C. for maximal metabolic suppression and preservation of the organ.

Another feature is to provide an outer container for enclosing the first container and wherein the first or inner container is spaced from the outer container to define continuous insulating air space between the containers. The organ receptacles are spaced from each other and from the walls of the inner container provided a chilling zone which is filled with a quantity of ice. The ice extends throughout a major portion of the height of each receptacle so as to continuously maintain the organ therein for chilling preservation at temperatures between 0° and 7° C., approximately for maximal metabolic suppression and preservation of the individual organs until transplant to a recipient.

Still another feature is to provide the inner and outer containers and the organ receptacles and their corresponding covers of a clear plastic material to permit visual examination thereof and wherein calibrated thermometers are mounted upon the interior of the receptacles to provide a visual and accurate measure of the temperature maintained with respect to the organ therein.

A further feature is to provide an improved organ hypothermic storage unit wherein there is provided an inner container having groups of spacing means upon the bottom wall thereof by which a plurality of organ receiving receptacles are spaced from each other and from the corresponding interior walls of the inner container so as to define a chilling zone within which is stored a quantity of ice for a portion of the height of such receptacles.

A still further feature includes spacing means upon the exterior of the inner container arranged with respect to the interior walls of the outer enclosing continer so that there is uniform spacing of the inner container relative to the enclosing outer container defining an insulating air space therebetween.

Another feature includes a removable cover for each receptacle and the containers and a depending peripheral flange adapted to sealingly nest down into the upper ends of the receptacles and containers respectively.

As a further feature the inner container is mounted upon the bottom of the outer container. Alternately it may be suspended within the outer container with the bottom wall of the inner container suspended above the bottom wall of the outer container to define an insulated air space therebetween.

A further feature contemplates the use of one or more drain pipes within the lower portion of the inner container which project through the corresponding apertures in the outer container to permit the escape of accumulating melting water from the inner container.

A further feature contemplates that the quantity of ice within the chilling zone within the inner container and surrounding the receptacles be maintained at a uniform level substantially the height of the receptacle or at least for two-thirds of its height, and wherein that level can be maintained by the addition of ice from time to time.

Another feature includes handles upon the ends of the inner container and upon the covers of the receptacles therein when the inner container is used alone without an outer container.

Another feature includes handles at opposite ends of the outer container when the inner container is nested therein by which the entire assembly may be transported from one supporting surface to another.

These and other features and objects wil be seen from the following Specification and claims in conjunction with the appended drawings.

THE DRAWINGS

It will be understood that the above drawings illustrate several preferred embodiments of the invention and that other embodiments are contemplated within the scope of the claims hereafter set forth.

DETAILED DESCRIPTION OF AN EMBODIMENT OF THE INVENTION

Figure 1:
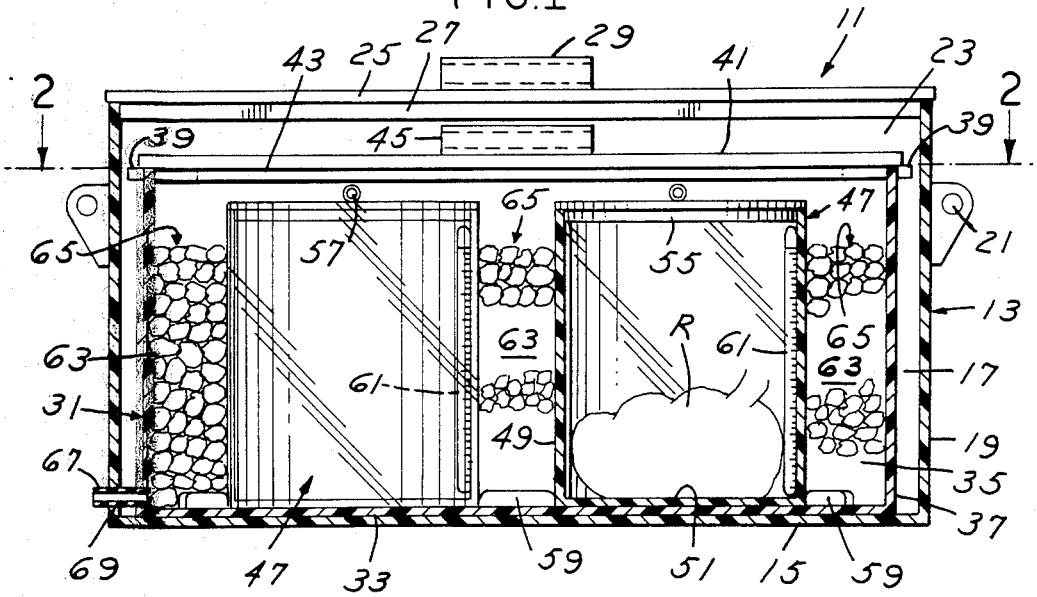
FIG. 1 is a vertical section of an organ hypothermic storage unit taken in the direction of arrows 1—1 of FIG. 2.
Figure 2:
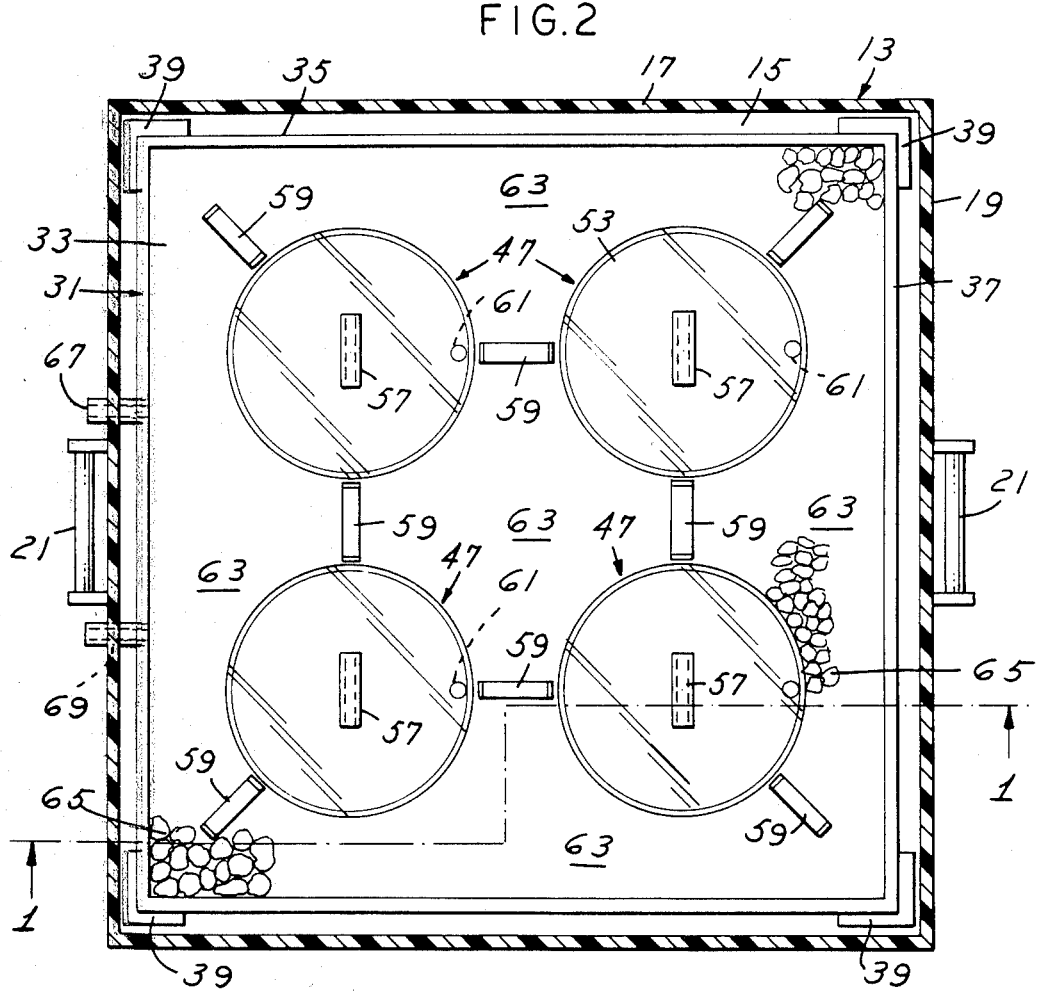
FIG. 2 is a plan section taken in the direction of arrows 2—2 of FIG. 1.

Referring to FIGS. 1 and 2, the present organ hypothermic storage unit is designated at 11 and includes an outer container 13, preferably of rectangular shape and constructed of a clear plastic material which will not cloud up at temperatures approaching 0° Centigrade. The container 13 may be constructed of polystyrene, polycarbonate plexiglass, ABS resins or any other plastic material which is clear and transparent at all times.

Outer container 13 includes upright side walls 17, opposed end walls 19 with handles 21 mounted upon and projecting from upper end portion of the end walls. The walls 17, 19 define an open top 23, FIG. 1, over which is positioned an elongated similarly shaped cover 25 having a depending peripheral sealing flange 27 which is snugly projected into the open top 23 in sealing engagement with the surrounding walls 17, 19.

Mounted upon cover 25 centrally thereof is a handle 29 to facilitate lifting thereof for access to the inner container 31. The container 31 is constructed of a similar clear plastic material and includes bottom all 33 which is supported upon the bottom wall 15 of container 13 in the embodiment shown in FIGS. 1 and 2. Container 31 includes side walls 35 and end walls 37.

Mounted upon the inner container 31 at its corners at the corresponding upper ends of the side and end walls 35 and 37 are right angular corner spacers 39 adapted for substantial registry with the interior walls of outer container 13. This is for centrally spacing the inner container 31 therein and for providing a continuous insulating air space therearound and between the containers 13 and 31. Cover 41 of the same clear plastic material overlies the open end of inner container 31 and includes a similar peripheral sealing flange 43 adapted for snug projection into the interior of the inner container 31 when the cover is positioned thereover, FIG. 1.

Container 31 and its cover 41 with handle 45 extend substantially the height of outer container 13 so that the inner container 31 is fully enclosed thereby, FIG. 1. Handle 45 facilitates access to the interior of container 31.

Organ receptacles 47 arranged in two laterally spaced pairs, FIG. 2, are mounted and spaced within container 31. Each receptacle 47 is adapted to individually receive an organ R for subsequent transplant, such as a kidney, a heart, a lung, a pancreas or other organ, human or animal. Each receptacle 47 includes a cylindrical body 49 having an open top constructed of similar clear plastic material, and a bottom wall 51 in registry with bottom wall 33 of the inner container 31. An organ is selectively stored within the respective receptacles 47 to be preserved and chilled for a limited time for subsequent transplant to a recipient.

Each of the cylindrical bodies 49 has mounted thereover a sealing lid 53 of similar plastic material which has an annular depending sealing flange 55 for cooperative nesting within the interior wall of the body 49. Each cover or lid 53 has a handle 57 to facilitate separation of such cover 53 from the corresponding receptacle 47 for access to the interior thereof.

The receptacles 47 of FIG. 2 are spaced from each other and uniformly spaced from the interior walls of inner container 31 by a plurality of groups of circularly arranged space stops 59 thereby defining a chilling zone 63 therein and around the exterior of the respective receptacles 47. A quantity of ice, preferably ice cubes or particles of irregular shape are projected within the chilling zone and within the inner container 31 for substantially the height of the receptacles 47, or for at least two-thirds of the height thereof as desired with the ice level being designated at 65, FIG. 1.

This level 65 must be maintained as melting ice is drained from the inner container 31 through the drain pipes 67, of which they may be a pair as in FIG. 2. These are arranged adjacent the bottom wall of the inner container 31 and extend through corresponding apertures 69 in the outer container 13.

Mounted in an upright position upon the interior of each of the receptacles 47 is a thermometer 61, preferably calibrated in centigrade between 0° and 40°, for illustration and wherein in accordance with the present invention the ice within the chilling zone 63 maintains the receptacles 47 and the organs R therein at temperatures above freezing normally in the range between 0° and 7° C. Normally the temperature is 4° C. approximately. This is believed to be the preferred temperature at which the organs R are maintained during storage within the respective receptacles 47 until used for subsequent transplant to a recipient.

FIRST MODIFICATION

Figure 3:
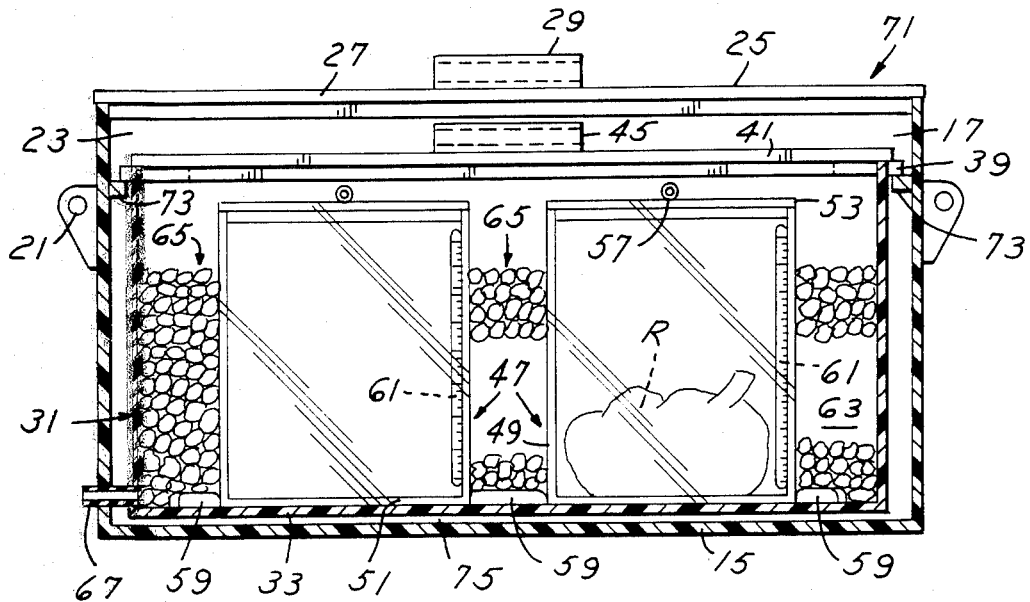
FIG. 3 is a vertical section similar to FIG. 1 of a modified storage unit with the inner container suspended within and above the bottom of the outer container.

A modified organ hypothermic storage unit 71 is shown in FIG. 3 which differs from the embodiment shown in FIG. 1 in that inner container 31 is supported and suspended within outer container 13 so as to define an air space 75 between the respective bottom walls of the containers.

For this purpose, mounted upon opposite ends of the outer container 13 upon the interior of end walls 19 are a pair of opposed inwardly directed shelves 73. These are spaced sufficiently above bottom wall 15 of the outer container 13 that when the inner container 31 and its corresponding corner spacers 39 are positioned so as to overlie and be supported upon the shelves 73, the bottom wall 33 is spaced from the bottom wall 15 defining space 75.

The inner container 31 is inwardly spaced uniformly with respect to the interior walls of outer container 13 and there is defined an air space 75 between the bottom walls of the containers providing an insulating air space which protectively encloses the inner container and assists in maintaining a chilling condition to prolong the life of the ice which is protectively spaced from ambient temperatures upon the exterior of the outer container.

SECOND MODIFICATION

Figure 4:
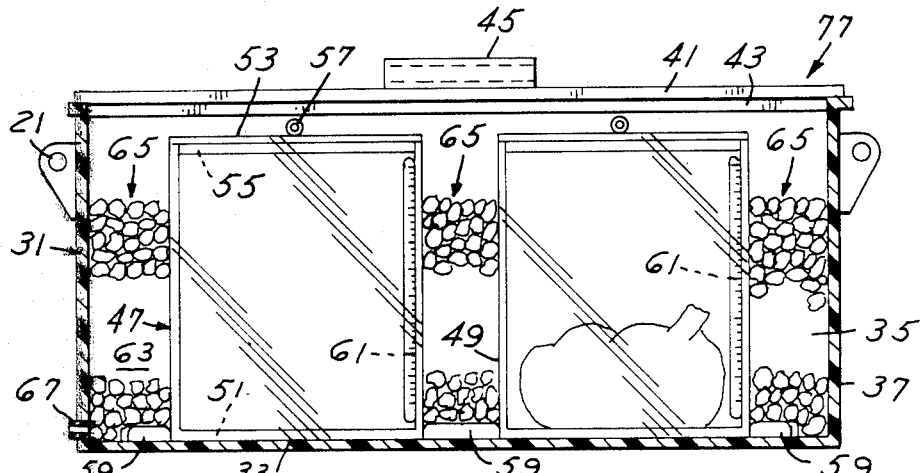
FIG. 4 is a similar view of a modified storage unit omitting the outer container.

A modified organ hypothermic storage unit 77 is shown in FIG. 4 which is the same as above described with respect to FIG. 1, except that only the inner container 31 is employed with its bottom wall 33 mountable upon a suitable support.

A plurality of groups of radially arranged spacer bosses 59 are secured upon bottom wall 33 of the inner container, FIGS. 1 through 4, with the respective spacer bosses arranged circularly and in groups to guidably receive and space the receptacles 47 with respect to each other and with respect to the interior walls of inner container 31. This provides a means by which the receptacles 47 when loaded with organs and closed by covers 53, may be manually positioned within the inner container 31 and guided into such position and spacing, FIG. 2. This provides uniform spacing between the receptacles 47 and the interior walls in the inner chamber to define the chilling zone 63, within which is stored a quantity of ice up to the level 65, FIG. 1. Under some circumstances it may be desired to immerse the organ within a suitable fluid upon the interior of the receptacles 47 which to a certain extent may permeate the respective cells or passages within the organ R stored protecting the organ R as is known in the art.

THIRD MODIFICATION

Figure 5:
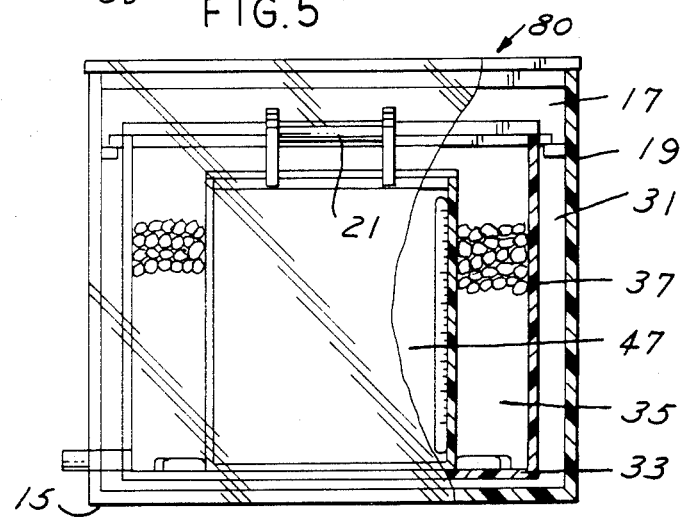
FIG. 5 is a transverse sectional view of another modified storage unit, constructed to hold only a pair of receptacle and provided with single or double containers.

The organ hypothermic storage units 11, 71 and 77 may each be modified to form storage unit 80 whereby the outer and inner containers are cut effectively in half or reduced in size as in FIG. 5 so as to hold only a pair of organ receptacles 47 rather than two pairs as discussed previously. The two receptacles 47 are spaced generally uniformly from the walls 35 and 37 of the modified inner receptacle 31. The walls 35 and 37 of the modified inner receptacle 31 are in turn generally uniformly spaced from the walls 17, 19 of the outer container 13 if such outer container is provided.

The two receptacle modified organ hypothermic storage unit 80 may have the bottom wall 33 of the inner container abutting the bottom wall 15 of the outer container as in FIG. 1 or spaced therefrom as in FIG. 3. Also the modified two receptacle storage unit may be used with only the modified inner container as in FIG. 4.

Having described my invention, reference should now be had to the following claims.

I claim:

1. An organ hypothermic storage unit comprising a transparent plastic first container having side, end and bottom walls and an open top;
    a transparent plastic cover removably sealed over said open top;
    at least a pair of transparent plastic receptacles adapted to receive an organ nested within said container, each receptacle including a cylindrical body having a bottom wall supported upon said container bottom wall, a side wall substantially the height of said container walls and an open top;
    a transparent plastic cover removably sealed thereover;
    a plurality of groups of circularly spaced guide stops upon the container bottom wall, with the stops in each group arranged in a circle, each group of stops receiving and locating a receptacle for spacing the receptacles from each other and from the adjacent walls of said container defining a chilling zone within said container and extending around each receptacle;
    an upright thermometer upon the interior side wall of each receptacle, visible through said wall;
    and a horizontal drain pipe extending through one wall of said container adjacent its bottom wall;
    said container adapted to receive and store a quantity of ice within said chilling zone for continuously maintaining an organ in any receptacle at a temperature between 0° and 7°, Centigrade approximately, for maximal metabolic suppression and preservation thereof until transplant to a recipient.

2. In the storage unit of claim 1, said temperature being 4° C. approximately.

3. In the storage unit of claim 1, opposed handles mounted upon said container end walls;
    and a handle upon each receptacle cover.

4. In the storage unit of claim 1, there being opposed pairs of laterally spaced receptacles within said container.

5. In the storage unit of claim 1, each of the covers having a depending peripheral flange snugly nested within the open tops of said container and receptacles respectively.

6. In the storage unit of claim 1, an outer transparent plastic container loosely receiving and enclosing said first transparent plastic container and having side, end and bottom walls and an open top;
    a transparent plastic cover removably sealed over said open top;
    the bottom wall of said first container resting upon the bottom wall of said outer container;
    said drain pipe extending through a corresponding wall of said outer container.

7. In the storage unit of claim 6, opposed handles mounted upon said outer container end walls;
    and a handle upon each receptacle cover.

8. In the storage unit of claim 6, right angular corner spacers mounted upon the corners of said first container adjacent the upper ends of its side and endwalls and projecting outwardly therefrom for centrally spacing said first container within said outer container and defining a continuous insulating air space between said containers.

9. In the storage unit of claim 1, an outer transparent plastic container loosely receiving and enclosing said first transparent plastic container and having side, end and bottom walls and an open top;
    a transparent plastic cover removably sealed over said open top;
    said drain pipe extending through a corresponding wall of said outer container;
    right angular corner spacers mounted upon the corners of said first container adjacent the upper ends of its side and end walls and projecting outwardly therefrom for centrally spacing said first container within said outer container and defining a continuous air space between said containers;
    and opposed inwardly directed shelves within said outer container mounted upon its end walls;
    said corner spacers being supported upon said shelves, with the bottom wall of said first container spaced above the bottom wall of said outer container defining an air space therebetween.

* * * * *